United States Patent
Taniguchi et al.

(10) Patent No.: US 7,053,393 B2
(45) Date of Patent: May 30, 2006

(54) ALIGNMENT APPARATUS FOR OBJECT ON STAGE

(75) Inventors: Yoshihisa Taniguchi, Okaya (JP); Shunsuke Kurata, Kamiina-gun (JP)

(73) Assignee: Olympus Corporation, Tokyo (JP)

( * ) Notice: Subject to any disclaimer, the term of this patent is extended or adjusted under 35 U.S.C. 154(b) by 300 days.

(21) Appl. No.: 10/454,320

(22) Filed: Jun. 4, 2003

(65) Prior Publication Data

US 2003/0222229 A1    Dec. 4, 2003

(30) Foreign Application Priority Data

Jun. 4, 2002   (JP) .............................. 2002-163263

(51) Int. Cl.
G01N 21/86   (2006.01)
(52) U.S. Cl. ................. 250/559.3; 250/559.4
(58) Field of Classification Search ............ 250/559.3, 250/559.33, 559.36, 548, 221, 559.4; 356/399, 356/400, 401; 414/935, 936
See application file for complete search history.

(56) References Cited

U.S. PATENT DOCUMENTS 5,807,062 A * 9/1998 Schultz et al. ........... 414/744.2
6,225,012 B1 * 5/2001 Nishi et al. ................ 430/22

FOREIGN PATENT DOCUMENTS

JP          8-215876        8/1996

* cited by examiner

Primary Examiner—Que T. Le
Assistant Examiner—Tony Lu
(74) Attorney, Agent, or Firm—Scully, Scott, Murphy & Presser, P.C.

(57) ABSTRACT

An object is held on a stage of an equipment, the stage is rotated in order to acquire a detection signal corresponding to a position of an outer peripheral edge of the object, a displacement of the object with respect to an alignment reference position is obtained based on this detection signal, and the stage is subjected to movement control so as to eliminate this displacement, thereby aligning the object.

15 Claims, 3 Drawing Sheets

ALIGNMENT APPARATUS FOR OBJECT ON STAGE

CROSS-REFERENCE TO RELATED APPLICATIONS

This application is based upon and claims the benefit of priority from the prior Japanese Patent Application No. 2002-163263, filed Jun. 4, 2002, the entire contents of which are incorporated herein by reference.

BACKGROUND OF THE INVENTION

1. Field of the Invention

The Present invention relates to an alignment apparatus which aligns a semiconductor wafer to a predetermined posture when taking out an object such as a semiconductor wafer accommodated in a storage container by a carriage robot and delivering it to an equipment such as an inspection apparatus.

2. Description of the Related Art

As an alignment apparatus for a semiconductor wafer, there is a technique disclosed in, e.g., Jpn. Pat. Appln. KOKAI Publication No. 8-215876. In this publication, a semiconductor wafer is taken out from a wafer carrier by a carriage robot and delivered to a pre-alignment apparatus. The pre-alignment apparatus irradiates a flat of the semiconductor wafer with a light beam and photo-electrically converts a part of it, thereby detecting a positional relationship between the flat and an axis X or Y in a rotating direction. Thereafter, the pre-alignment apparatus performs positioning of the semiconductor wafer in the rotating direction based on the detected positional relationship between the flat and the axis X or Y in the rotating direction. The positioned semiconductor wafer is again taken out from the pre-alignment apparatus by the carriage robot, and mounted on a stage of a processing apparatus.

In the above-described publication, however, the pre-alignment apparatus and the processing apparatus are separately provided. Therefore, the semiconductor wafer must be carried from a wafer carrier to the pre-alignment apparatus by the carriage robot, and then carried from the pre-alignment apparatus to the processing apparatus after positioning of the semiconductor wafer. Accordingly, it takes a time to perform each carriage, and also takes a time until the semiconductor wafer is processed.

In a manufacturing field of the semiconductor wafer, there are requests to reduce a tact time of manufacturing/processing. Thus, the time required for alignment of the semiconductor wafer should be shortened.

Alternatively, since the semiconductor wafer is carried from the pre-alignment apparatus to the processing apparatus by the carriage robot after positioning of the semiconductor wafer, there is a possibility that a deviance is generated in positioning of the semiconductor wafer.

BRIEF SUMMARY OF THE INVENTION

According to a major aspect of the present invention, there is provided an alignment apparatus comprising: a stage which is provided to an equipment which performs processing or inspection with respect to an object, holds the object delivered by a carriage robot and effects a movement operation of the object in a direction XY and a rotation operation in a rotating direction; a sensor which detects an outer peripheral edge of the object rotating by the rotation operation of the stage; and an alignment control portion which obtains a displacement of the object relative to an alignment reference position based on positional information of the outer peripheral edge detected by the sensor, controls to move the stage so as to eliminate this displacement and aligns the object to the alignment reference position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment according to the present invention will now be described hereinafter with reference to the accompanying drawings.

Figure 1:
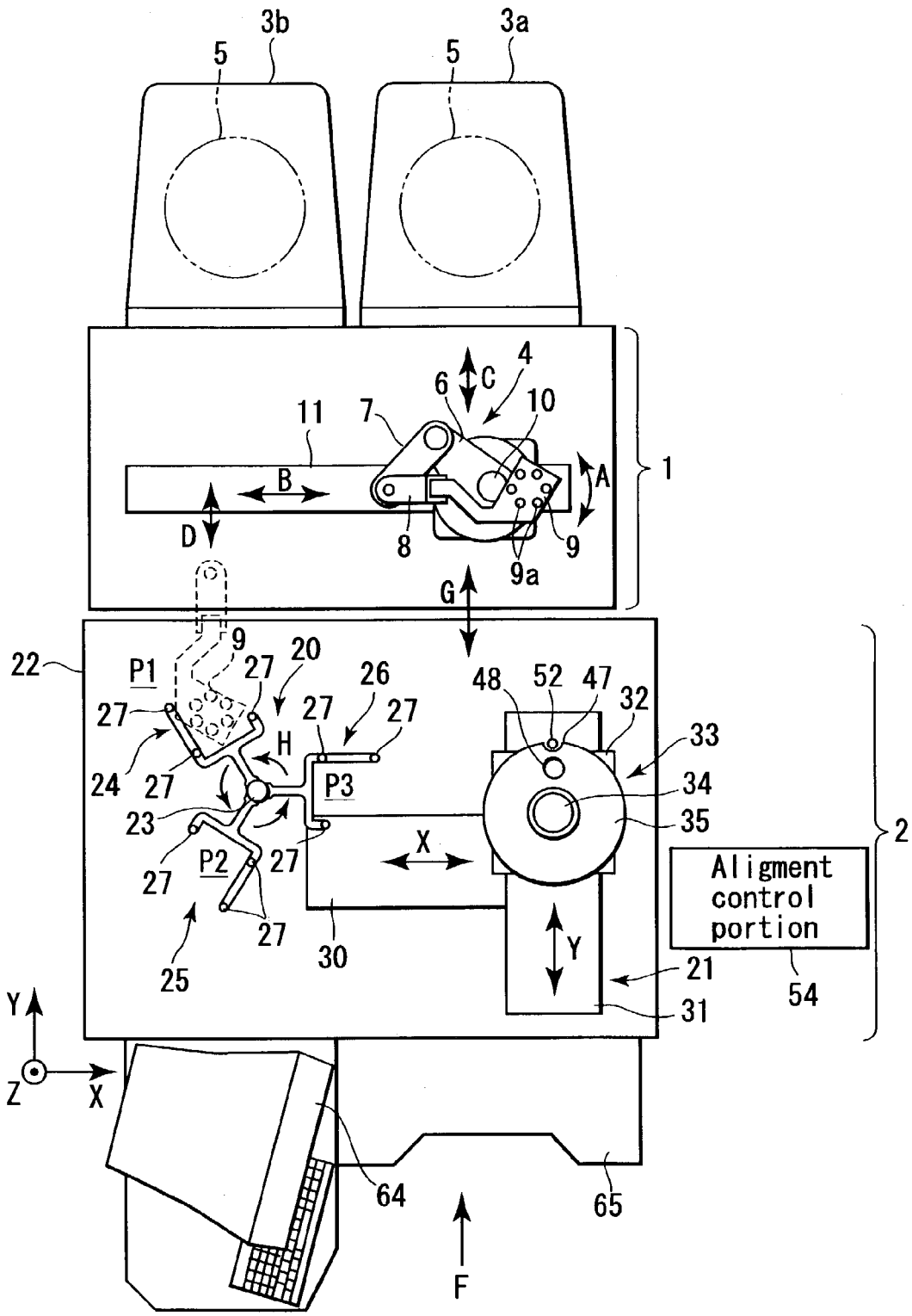
FIG. 1 is a block diagram showing a wafer inspection apparatus to which an embodiment of an alignment apparatus according to the present invention is applied.

FIG. 1 is a block diagram showing a wafer inspection apparatus to which an alignment apparatus is applied. The wafer inspection apparatus consists of a loader apparatus 1 and an inspection apparatus 2. The loader apparatus 1 is constituted by wafer carriers 3a and 3b and a carriage robot 4. The respective wafer carriers 3a and 3b accommodate therein a plurality of semiconductor wafers 5 in the vertical direction with a predetermined pitch. Of the respective semiconductor wafers 5, the semiconductor wafer 5 which is yet to be inspected is accommodated in, e.g., the wafer carrier 3a, and the inspected semiconductor wafer 5 is accommodated in the wafer carrier 3b.

A carriage robot 4 takes out the uninspected semiconductor wafer 5 accommodated in the wafer carrier 3a, delivers it to the inspection apparatus 2, receives the semiconductor wafer 5 which has been already inspected by the inspection apparatus 2 and accommodates it in the wafer carrier 3b.

The carriage robot 4 interlocks three connecting arms (which will be referred to as articulated arms hereinafter) 6 to 8 and thereby constitute articulated arms. A hand 9 is connected to the end side of the articulated arms 6 to 8. A plurality of suction holes 9a are provided to the hand 9. The hand 9 sucks and holds the semiconductor wafer 5. The hand 9 moves forward or backward by expansion and contraction operations of the articulated arms 6 to 8. The base side of the articulated arms 6 to 8 can rotate in a direction indicated by an arrow A around an axial direction with respect to a rotary shaft 10.

The carriage robot 4 is provided so as to be capable of moving in a direction indicated by an arrow B by a movement mechanism 11.

The inspection apparatus 2 fetches an image of a surface of the semiconductor wafer 5 enlarged by a microscope 61, and acquires a type or a size of a defective part on the surface of the semiconductor wafer 5.

A swiveling arm 20 and an XYθ stage 21 are provided on a counter 22 of the inspection apparatus 2. The swiveling arm 20 is provided on the left side seen from a front side F in the inspection apparatus 2. The XYθ stage 21 is provided on the right side seen from the front side F in the inspection apparatus 2.

A set position of the swiveling arm 20 is on a carriage path for the semiconductor wafer 5 between the carriage robot 4 and the XYθ stage 21. The swiveling arm 20 acts as a buffer holding portion which holds a plurality of, e.g., two semiconductor wafers 5.

The swiveling arm 20 has a rotary shaft 23 and three carriage arms 24 to 26 provided at equal angles (e.g., 120 degrees) with respect to the rotary shaft 23. A hand formed into a substantial L shape is integrally provided at an end of each of the respective carriage arms 24 to 26. A plurality of suction holes (wafer chucks) 27 are formed to each of the carriage arms 24 to 26. Each suction hole 27 is connected to a suction apparatus such as a suction pump.

The swiveling arm 20 integrally moves up and down the three carriage arms 24 to 26 by providing the rotary shaft 23 so as to be capable of moving upwards and downwards.

The swiveling arm 20 rotates in, e.g., a counterclockwise direction (direction indicated by an arrow H) in the drawing around the rotary shaft 23. As a result, the three carriage arms 24 to 26 circulate at a wafer delivery position $P_1$, a macro inspection position $P_2$ and a micro inspection delivery position $P_3$.

At the wafer delivery position $P_1$, the semiconductor wafer 5 is delivered between the carriage robot 4 and the swiveling arm 20.

At the macro inspection position $P_2$, the macro inspection is carried out with respect to the semiconductor wafer 5. In the macro inspection, the semiconductor wafer 5 is irradiated with the light, the scattered light is observed, and irregularities in film, a large defective position and others on the semiconductor wafer 5 are visually detected.

At the micro inspection delivery position $P_3$, the semiconductor wafer 5 is delivered between any one of the respective carriage arms 24 to 26 and the XYθ stage 21.

The XYθ stage 21 consists of an X axis slider 30, an X axis stage 31, a Y axis stage 32 and a holding stage 33. The X axis stage 31 is provided so as to be capable of moving on the X axis slider in the direction of the axis X. The Y axis stage 32 is provided so as to be capable of moving on the X stage 31 in the direction of the axis Y.

The holding stage 33 has a rotary stage 34 and a suction holding stage 35. The rotary stage 34 is provided so as to be capable of moving up and down and rotating. The rotary stage 34 sucks and holds the semiconductor wafer 5.

The suction holding stage 35 is provided on the outer periphery of the rotary stage 34, and formed into an annular shape (a so-called a donut shape) in order to suck and hold the semiconductor wafer 5.

The rotary stage 34 and the suction holding stage 35 are provided on a concentric circle. The rotary stage 34 is formed to, e.g., approximately φ80 mm, and the suction holding stage 35 is formed to, e.g., approximately φ300 mm.

Figure 2:
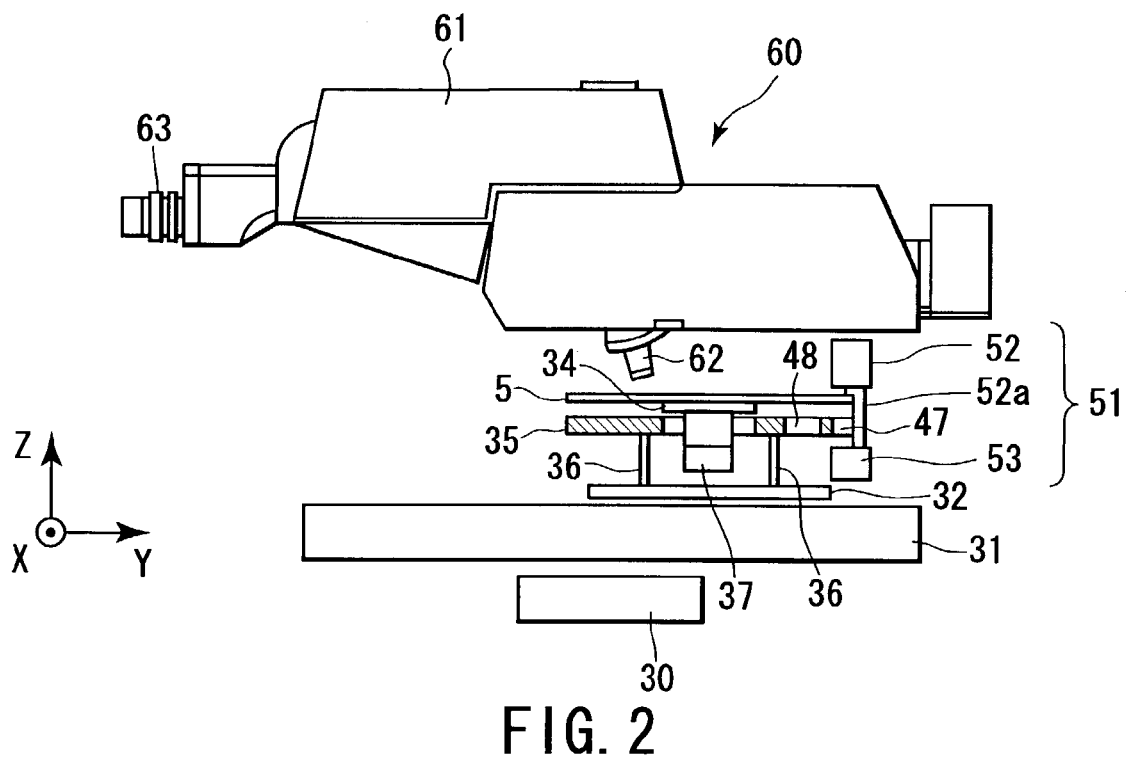
FIG. 2 is a view showing a positional relationship between a light projecting element and a light receiving element relative to a semiconductor wafer having a diameter of 300 mm in the embodiment of the alignment apparatus according to the present invention.
Figure 3:
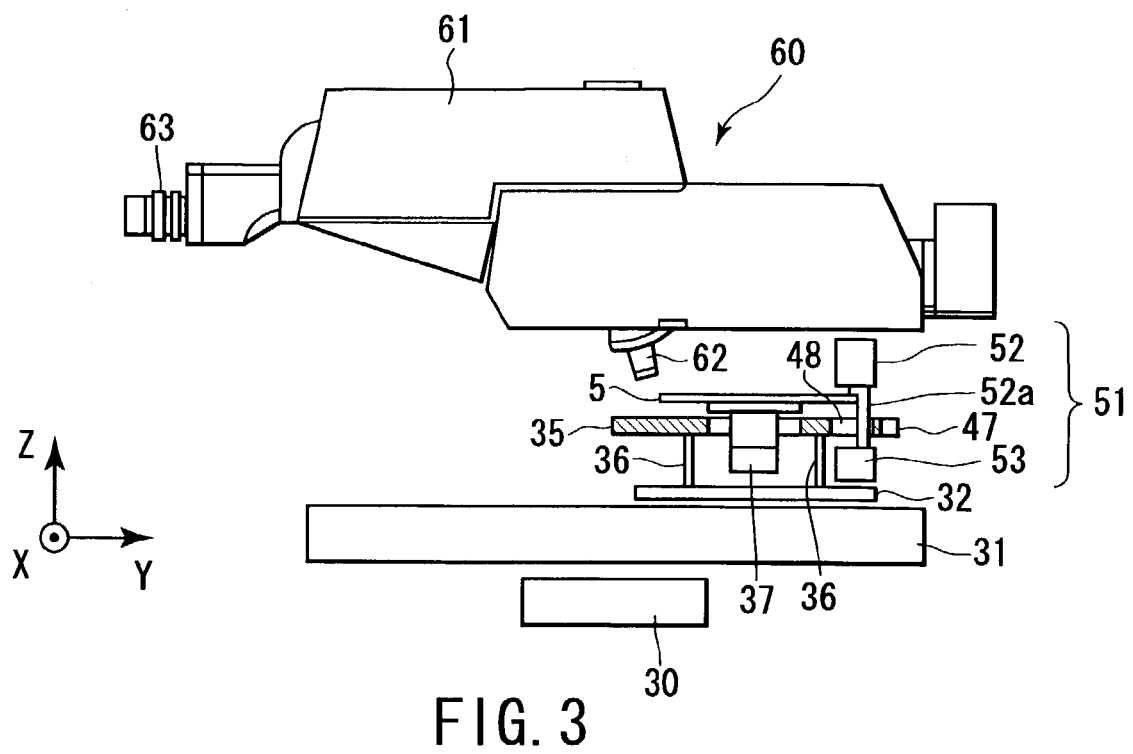
FIG. 3 is a view showing a positional relationship between a light projecting element and a light receiving element relative to a semiconductor wafer having a diameter of 200 mm in the embodiment of the alignment apparatus according to the present invention.

FIGS. 2 and 3 are block diagrams showing the XYθ stage 21 from the lateral direction. The suction holding stage 35 is supported on the Y axis stage 32 through supports 36. The rotary stage 34 is provided to a rotary shaft of a motor 37. The rotary stage 34 and the motor 37 are integrally provided so as to be capable of moving up and down.

Figure 4:
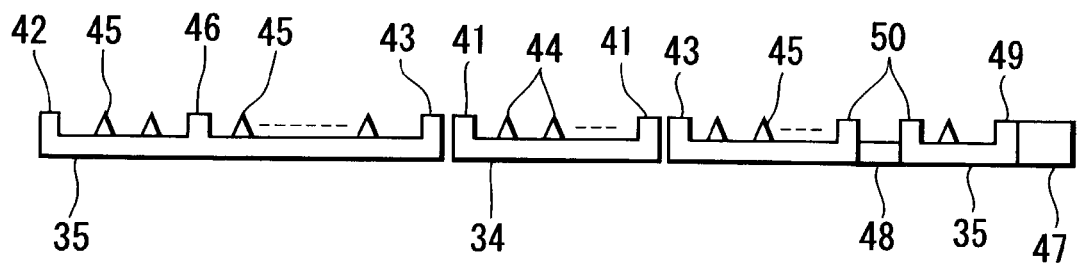
FIG. 4 is a cross-sectional view of a rotary stage and suction holding in the embodiment of the alignment apparatus according to the present invention.

FIG. 4 is a cross-sectional view showing the rotary stage 34 and the suction holding stage 35. A bank 41 is formed on the outer peripheral edge of the rotary stage 34. Respective banks 42 and 43 are formed on the outer peripheral edge and the inner peripheral edge of the suction holding stage 35. The respective banks 41 to 43 are formed to have the same height.

Many pins 44 are formed on the bottom surface of the rotary stage 34. Many pins 45 are formed on the bottom surface of the suction holding stage 35. The respective pins 44 and 45 are formed to have the same height as that of the respective banks 41 to 43.

The bank 42 is formed into the same shape as the outer peripheral shape of the semiconductor wafer 5 having a diameter of 300 mm in order to suck and hold the semiconductor wafer 5 having the diameter of 300 mm. The bank 42 and the bank 43 on the inner peripheral edge form an annular full suction pad.

A circular convex portion 46 is formed between the respective banks 42 and 43 of the suction holding stage 35. The convex portion 46 is formed into the same shape as the outer peripheral shape of the semiconductor wafer 5 having the diameter of 200 mm in order to suck and hold the semiconductor wafer 5 having the diameter of 200 mm. The convex portion 46 is also formed to have the same height as the respective banks 42 and 43. The convex portion 46 and the bank 43 on the inner peripheral edge form an annular full suction pad.

Many suction holes are formed on the rotary stage 34 and the suction holding stage 35. Each suction hole communicates with the suction apparatus.

At the time of inspection of the semiconductor wafer 5, when the semiconductor wafer 5 having the diameter of 300 mm is mounted on the suction holding stage 35, a sealed space is formed on the suction holding stage 35 by the semiconductor wafer 5 and the respective banks 42, 43 and 46. The sealed space has a negative pressure by the suction operation of the suction apparatus. As a result, the semiconductor wafer 5 is assuredly fully sucked and held on the suction holding stage 35. The semiconductor wafer 5 is horizontally held by the respective banks 42, 43 and 46 and many pins 45.

At the time of inspection of the semiconductor wafer 5, when the semiconductor wafer 5 having the diameter of 200 mm is mounted on the suction holding stage 35, a sealed space is formed on the suction holding stage 35 by the semiconductor wafer 5, the bank 43 and the convex portion 46. The sealed space has a negative pressure by the suction operation of the suction apparatus. As a result, the semiconductor wafer 5 is assuredly fully sucked and held on the suction holding stage 35. The semiconductor wafer 35 is horizontally held by the bank 43, the convex portion 46 and many pins 45.

A notch portion 47 is formed at an outer peripheral part of the suction holding stage 35. The notch portion 47 is formed in order to detect a wafer edge of the semiconductor wafer 5 having the diameter of 300 mm.

A hole 48 is formed at a position on the suction holding stage 35 which corresponds to a wafer edge position of the semiconductor wafer 5. The hole 48 is formed in order to detect a wafer edge of the semiconductor wafer 5 having the diameter of 200 mm.

The notch portion 47 and the hole 48 are formed in the radial direction of the rotary stage 34 and the suction holding stage 35. It is to be noted that respective banks 49 and 50 are formed on the outer peripheries of the notch portion 47 and the hole 48. The respective banks 49 and 50 are formed to have the same height as another bank, e.g., the bank 43.

A sensor 51 is provided at an alignment position on the inspection apparatus 2 as shown in FIGS. 2 and 3. The sensor 51 fixes a light projecting element 52 and a light receiving element 53 so as to be opposed to each other. The light projecting element 52 projects, e.g., a fixed quantity of light 52a. The light projecting element 52 is, e.g., a light emitting diode. The light receiving element 53 outputs a detection signal corresponding to a light quantity which is projected from the light projecting element 52 and incident thereupon without being blocked by the wafer edge of the semiconductor wafer 5. The light receiving element 53 is, e.g., a photodiode.

In FIG. 2, the semiconductor wafer 5 having the diameter of 300 mm is sucked on the rotary stage 34. When aligning the semiconductor wafer 5, the rotary stage 34 moves up by a predetermined distance above the height position of the suction holding stage 35. The notch portion 47 is positioned in a detection area of the light projecting element 52 and the light receiving element 53 by movement of the X axis stage 31 and the Y axis stage 32 in the direction of the axis XY. The detection area of the light projecting element 52 and the light receiving element 53 is a passage area of the light 52a projected from the light projecting element 52.

In FIG. 3, the semiconductor wafer 5 having the diameter of 200 mm is sucked on the rotary stage 34. When aligning the semiconductor wafer 5, the rotary stage 34 moves up by a predetermined distance above the height position of the suction holding stage 35. The hole 48 is positioned in the detection area of the light projecting element 52 and the light receiving element 53 by movement of the X axis stage 31 and the Y axis stage 32 in the direction of the axis XY.

Figure 5:
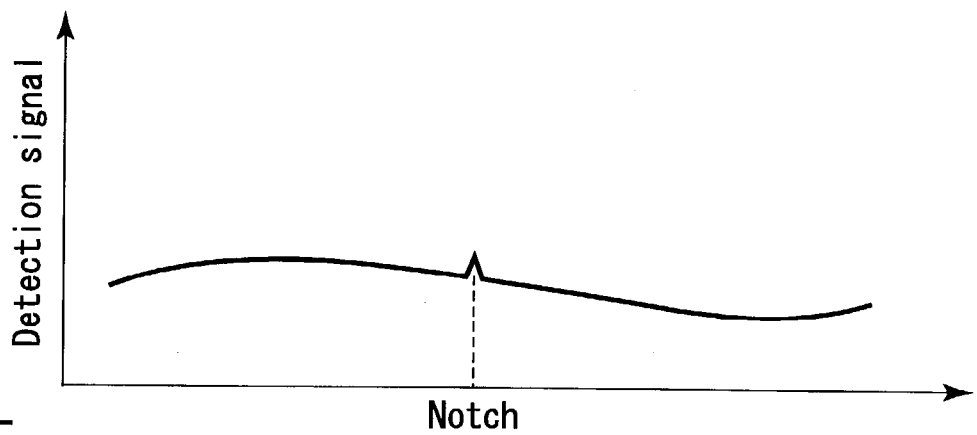
FIG. 5 is a view showing an example of a detection signal outputted from a sensor in the embodiment of the alignment apparatus according to the present invention.

FIG. 5 shows an example of a detection signal outputted from the sensor 51. The detection signal indicates a signal level change corresponding to a light quantity which has entered the light receiving element 53 without being blocked by the wafer edge of the semiconductor wafer 5 in the light 52a projected from the light projecting element 52.

The signal level change will now be described. It is often the case that the semiconductor wafer 5 sucked on the rotary stage 34 deviates from a reference position of alignment. The reference position of alignment is based on a central position of the rotary stage 34, semiconductor wafer 5 and a direction of the notch (or an original flat). When the semiconductor wafer 5 deviates from the reference position of alignment and rotates in this state, the semiconductor wafer 5 rotates in the eccentric state.

Then, in the detection area of the light projecting element 52 and the light receiving element 53, a wafer edge position of the semiconductor wafer 5 oscillates in accordance with a quantity of eccentricity of the semiconductor wafer 5. As a result, a quantity of the incident light on the light receiving element 53 varies. It is to be noted that the quantity of the incident light upon the light receiving element 53 is increased and a signal level of the detection signal becomes high in the notch part of the semiconductor wafer 5.

An alignment control portion 54 receives the detection signal outputted from the sensor 51, and obtains positional information of the wafer edge of the semiconductor wafer 5 based on the signal level of the detection signal and a rotation angle of the rotary stage 34. The wafer edge positional information is based on a central position of the semiconductor wafer 5 and the direction of the notch.

The alignment control portion 54 compares an alignment reference position of the semiconductor wafer 5 and the wafer edge positional information, and calculates a displacement of the semiconductor wafer 5 relative to the alignment reference position in units of, e.g., mm in the direction X and mm in the direction Y. The alignment reference position of the semiconductor wafer 5 is set in the alignment control portion 54 by an operator.

The alignment control portion 54 controls to move the X axis stage 31 and the Y axis stage 32 of the XYθ stage 21 in the directions of the axis X and the axis Y in accordance with displacement data of the semiconductor wafer 5 relative to the alignment reference position.

As shown in FIGS. 2 and 3, an inspection portion 60 is provided above the XYθ stage 21. The inspection portion 60 has a microscope 61. The microscope 61 has an object lens 62 and an eyepiece 63. An image pickup apparatus such as a CCD can be attached to the microscope 61. The image pickup apparatus picks up an image of the semiconductor wafer 5 enlarged by the microscope 61. The enlarged image of the semiconductor wafer 5 is displayed in a monitor apparatus 64.

An operation portion 65 is provided on a front side F of the inspection apparatus 2. The operation portion 65 effects an operation to inspect the semiconductor wafer 5, an operation to input an inspection result of the semiconductor wafer 5 and an operation to input various kinds of data such as data concerning the operation of the entire inspection apparatus 2.

The operation of the apparatus having the above-described structure will now be described.

The carriage robot 4 extends the articulated arms 6 to 8 and the hand 9 in a direction indicated by an arrow C, sucks and holds the uninspected semiconductor wafer 5 in the wafer carrier 3a, and moves to and stops at the wafer delivery position $P_1$ while retracting the articulated arms 6 to 8 and the hand 9.

Then, the carriage robot 4 extends the articulated arms 6 to 8 and the hand 9 in a direction indicated by an arrow D, and moves the sucked and held semiconductor wafer 5 above the carriage arm 24.

Subsequently, the swiveling arm 20 integrally moves up the three carriage arms 24 to 26 by upward movement of the rotary shaft 23. As a result, the carriage arm 24 receives the semiconductor wafer 5 held on the hand 9. At the same time, the carriage arm 24 sucks and holds the semiconductor wafer 5 by start of suction of each suction hole 27.

At this moment, if some semiconductor wafers 5 have been already held on the swiveling arm 20, the carriage arm 25 receives the macro inspected the semiconductor wafer 5.

At the micro inspection delivery position $P_3$, the carriage arm 26 receives the micro inspected the semiconductor wafer 5. The semiconductor wafer 5 is subjected to the micro inspection in the inspection portion 60.

Then the swiveling arm 20 rotates around the rotary shaft 23 in the counterclockwise direction (direction indicated by an arrow H) in the drawing. The swiveling arm 20 moves down. As a result, the carriage arm 24 moves to the macro inspection position $P_2$. The carriage arm 25 moves to the micro inspection delivery position $P_3$. The carriage arm 26 moves to the wafer delivery position $P_1$.

Description will now be given as to delivery of the semiconductor wafer 5 at the micro inspection delivery position $P_3$ and the alignment operation of the semiconductor wafer 5.

The XYθ table 21 moves up the rotary stage 34 beyond the height position of the suction holding stage 35.

Then, with the rotary stage 34 being moved up, the XYθ table 21 operates to move the X axis stage 31 and the Y axis stage 32, moves the rotary stage 34 to the micro inspection delivery position $P_3$, and enters the standby mode.

The swiveling arm 20 causes the carriage arm 25 which holds the semiconductor wafer 5 which has been already subjected to the macro inspection to stop at the micro inspection delivery position $P_3$ by allowing circulation movement of the three carriage arms 24 to 26. As a result, the rotary stage 34 is positioned at the delivery position (micro inspection delivery position $P_3$) in the substantial L shape of the carriage arm 26.

Thereafter, the swiveling arm 20 moves down the three carriage arms 24 to 26. As a result, the semiconductor wafer 5 on the carriage arm 25 is delivered to the central part of the rotary stage 34. At this moment, the suction operation of the carriage arm 25 is canceled, and the suction operation of the rotary stage 34 is started.

Then, with the rotary stage 34 which is sucking and holding the semiconductor wafer 5 being moved up, the XYθ table 21 operates to move the X axis stage 31 and the Y axis stage 32. With the movement, the XYθ table 21 moves the rotary stage 34 which is sucking and holding the semiconductor wafer 5 to the alignment position.

At the alignment position, in case of the semiconductor wafer 5 having the diameter of 300 mm, the rotary stage 34 moves the notch portion 47 to a position where it is matched with the optical axis of the light projecting element 52 and the light receiving element 53 as shown in FIG. 2. The wafer edge of the semiconductor wafer 5 having the diameter of 300 mm is arranged on the optical axis of the light projecting element 52 and the light receiving element 53 running through the notch portion 47.

When the rotary stage 34 rotates at a uniform velocity in this arrangement state, the light 52a projected from the light projecting element 52 is partially blocked by the wafer edge of the rotating semiconductor wafer 5, and enters the light receiving element 53 through the notch portion 47. As shown in FIG. 5, the light receiving element 53 outputs a detection signal indicative of a level change corresponding to a light reception quantity of the received light 52a.

On the other hand, in case of the semiconductor wafer 5 having the diameter of 200 mm, as shown in FIG. 3, the rotary stage 34 moves the hole 48 to a position where it is matched with the optical axis of the light projecting element 52 and the light receiving element 53. The wafer edge of the semiconductor wafer 5 having the diameter of 200 mm is arranged on the optical axis of the light projecting element 52 and the light receiving element 53 running through the hole 48.

Thereafter, when the semiconductor wafer 5 rotates being eccentric with respect to a predetermined posture like the above description, the light receiving element 53 outputs a detection signal indicative of a level change corresponding to a light reception quantity of the received light 52a as shown in FIG. 5.

The alignment control portion 54 obtains a displacement of the semiconductor wafer 5 with respect to the alignment reference position based on the signal level of the detection signal outputted from the sensor 51 and a rotation angle of the rotary stage 34, and controls to move the XYθ stage 21 in accordance with this displacement.

As a result, the semiconductor wafer 5 is positioned at the alignment reference position.

Then, the rotary stage 34 which is sucking and holding the semiconductor wafer 5 moves down beyond the height position of the suction holding stage 35, and cancels the suction operation relative to the semiconductor wafer 5.

At the same time, the suction holding stage 35 starts the suction operation with respect to the semiconductor wafer 5. As a result, the semiconductor wafer 5 is entirely sucked on the suction holding stage 35.

Then, the image pickup apparatus picks up an image of the semiconductor wafer 5 enlarged through the microscope 61. The image of the semiconductor wafer 5 is displayed in the monitor apparatus 64. As a result, the micro inspection of the semiconductor wafer 5 is effected. It is to be noted that focusing of the object lens 62 in the microscope 61 relative to the semiconductor wafer 5 is adjusted by moving up and down the suction holding stage 35.

Upon completion of the micro inspection, the suction holding stage 35 stops the suction operation with respect to the semiconductor wafer 5. At the same time, the rotary stage 34 moves up and starts the suction operation, thereby sucking and holding the semiconductor wafer 5.

Subsequently, the XYθ stage 21 operates to move the X axis stage 31 and the Y axis stage 32, and moves the semiconductor wafer 5 to the micro inspection delivery position $P_3$.

At this moment, the carriage arm 25 is below the height position of the semiconductor wafer 5 on the rotary stage 34. The swiveling arm 20 moves up and mounts the semiconductor wafer 5 on the carriage arm 25.

The swiveling arm 20 again allows circulation movement of the three carriage arms 24 to 26 at the micro inspection delivery position $P_3$, the wafer delivery position $P_1$ and the macro inspection position $P_2$.

As described above, according to the embodiment, since the semiconductor wafer 5 does not have to be carried between the pre-alignment apparatus and the inspection apparatus by the carriage robot, the time to perform the micro inspection relative to the semiconductor wafer 5 can be shortened by a time required for the carriage. As a result, it is possible to satisfy a reduction in a tact time in manufacture required in a manufacture field of the semiconductor wafer 5 and a reduction in the defect inspection time of the semiconductor wafer 5 involved by manufacture.

Further, since the pre-alignment apparatus does not have to be additionally provided, the wafer inspection apparatus can be minimized by an amount corresponding to the space in which the pre-alignment apparatus is provided.

Since the alignment of the semiconductor wafer 5 also functions as the rotary stage 34 of the inspection apparatus 2, the micro inspection relative to the semiconductor wafer 5 can be performed in the inspection apparatus 2 immediately after the alignment. Therefore, since it is not necessary to carry the semiconductor wafer 5 after the alignment, the micro inspection can be effected while keeping the posture of the highly accurately aligned semiconductor wafer 5.

A plurality of the semiconductor wafers 5 are not positioned and they are accommodated at different positions in the wafer carrier 3a. When the semiconductor wafers 5 taken out from the wafer carrier 3a are circulated to the micro inspection delivery position P₃ by the respective carriage arms 24 to 26, the respective semiconductor wafers 5 are displaced with respect to the alignment reference position, and a displacement quantity becomes large.

In such a case, by enlarging the detection area of the light projecting element 52 and the light receiving element 53 for the wafer edge of the semiconductor wafer 5, the sensor 51 can detect the oscillation of the wafer edge of the semiconductor wafer 5 even if a displacement quantity of the semiconductor wafer 5 is large. As a result, it is possible to accurately obtain a deviation of the semiconductor wafer 5 from the alignment reference position and a deviation in the direction of the notch. Consequently, the semiconductor wafer 5 can be highly accurately aligned.

If a displacement quantity of the semiconductor wafer 5 is large, there is a method by which the semiconductor wafer 5 is pre-aligned by the carriage robot 4 or the swiveling arm 20 and then delivered to the rotary stage 34, for example. Even if this method is not adopted, enlarging the detection area of the light projecting element 52 and the light receiving element 53 enables alignment of the semiconductor wafer 5 without performing pre-alignment.

Since the swiveling arm 20 circulates the three carriage arms 24 to 26 to the wafer delivery position P₁, the macro inspection position P₂ and the micro inspection delivery position P₃, it can be caused to function as a buffer holding portion which holds one semiconductor wafer 5 on the upstream side of circulation from the inspection apparatus 2. As a result, upon completion of the micro inspection relative to the semiconductor wafer 5, the inspection apparatus 2 can immediately receive the next semiconductor wafer 5 from one carriage arm 24, 25 or 26, thereby reducing the time interval of the micro inspection for each semiconductor wafer 5.

The swiveling arm 20 not only performs buffer holding of a plurality of the semiconductor wafers 5, but it can sequentially carry out the macro inspection for each semiconductor wafer 5 at the macro inspection position P₂ before the micro inspection.

Since the notch portion 47 and the hole 48 are formed to the suction holding stage 35, it is possible to cope with alignment of the respective semiconductor wafers 5 having the diameter of 300 mm and the diameter of 200 mm. It is to be noted that forming a plurality of the holes 48 enables alignment of the semiconductor wafers 5 having a plurality of diameter sizes.

It is to be noted that the present invention is not restricted to the above-described embodiment, and various modifications can be carried out without departing from the scope of the invention on an embodying stage.

Figure 6:
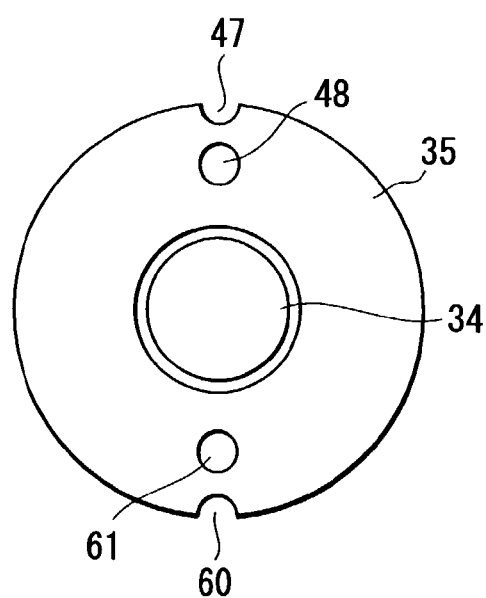
FIG. 6 is a view showing a modification of a sensor arrangement of the alignment apparatus according to the present invention.

For example, as shown in FIG. 6, a notch portion 60 and a hole 61 are formed at opposed positions through the center of the holding stage 33 from the notch portion 47 and the hole 48. A sensor 51 which detects the wafer edge of the semiconductor wafer 5 is additionally provided to the notch portion 60 and the hole 61.

If a pair of the sensors 51 are provided, it is good enough to rotate the rotary stage 34 at 180 degrees at the time of alignment. As a result, the inspection time of the semiconductor wafer 5 can be further reduced. Incidentally, if not only a pair but a plurality of the sensors 51 are provided, a rotation angle of the rotary stage 34 in alignment can be reduced, thus further shortening the inspection time of the semiconductor wafer 5.

The sensor 51 may be constituted by a combination of a light source which emits a slit light beam and a line sensor. In this case, the slit light beam is emitted in a direction vertical to the wafer edge of the semiconductor wafer 5. The line sensor detects a change in an incident position of the slit light beam corresponding to a wafer edge position which oscillates due to the eccentricity of the semiconductor wafer 5. The alignment control portion 54 receives a detection signal corresponding to the incident position of the slit light outputted from the sensor 51, and calculates and obtains a deviation of a central position of the semiconductor wafer 5 from the alignment reference position and a deviation in the direction of the notch or the original flat based on this detection signal and the rotation angle of the rotary stage 34.

The sensor 51 may be of a reflection type which projects the light onto the wafer edge of the semiconductor wafer 5 and receives the reflected light from the wafer edge.

The sensor 51 may be attached anywhere within a substrate movement range E. It is good to set an attachment position of the sensor 51 in such a manner that a distance from the alignment position to the micro inspection position becomes minimum in the inspection apparatus 2.

Furthermore, the attachment position of the sensor 51 may be provided on the Y axis stage 32. In this case, the rotary stage 34 is rotated while moving the semiconductor wafer 5 is moved from the macro inspection position P₂ to the inspection apparatus 2 by movement of the Y axis stage 32. In this period, the positional information of the wafer edge position of the semiconductor wafer 5 can be obtained. The inspection time of the semiconductor wafer 5 can be further reduced.

The swiveling arm 20 may be constituted by two carriage arms.

The swiveling arm 20 may be eliminated, and the semiconductor wafer 5 may be directly delivered onto the rotary stage 34 from the carriage robot 4. In this case, if, e.g., an L-shaped or U-shaped hand 9 of the carriage robot 4 is used, the semiconductor wafer 5 can be delivered to/from the rotary stage 34.

Directly delivering the semiconductor wafer 5 onto the rotary stage 34 can reduce the movement distance of the XYθ stage 21, thereby shortening the inspection time of the semiconductor wafer 5 by this reduced distance.

The holding stage 33 may be constituted by only the rotary stage 34. In this case, the rotary stage 34 having, e.g., φ80 mm is used. The sensor 51 may be attached anywhere within the substrate movement range E. If the semiconductor wafer 5 has, e.g., the diameter of 300 mm or the diameter of 200 mm, it is good enough to move the rotary stage 34 and move the wafer edge of the semiconductor wafer 5 to the detection area of the sensor 51.

The apparatus according to the present invention can be applied for alignment of the semiconductor wafer 5 in various kinds of equipments such as a measuring apparatus which measures a line width or the like of the semiconductor wafer 5, a pattern inspection apparatus, a stepper and others. The apparatus according to the present invention can be applied for alignment of various kinds of objects as well as the semiconductor wafer 5.

What is claimed is:

1. An alignment apparatus comprising:
   a stage which is provided in an inspection equipment which performs inspection with respect to an object, and also functions as a stage of the inspection equipment, holds the object delivered by a carriage robot, and carries out a movement operation with respect to the object in a direction XY and a rotation operation in a rotational direction;

a sensor which detects an outer peripheral edge of the object rotating by the rotation operation of the stage; and an alignment control portion which obtains a central position and an arrangement direction of the object based on positional information of the outer peripheral edge detected by the sensor, acquires a displacement quantity of the central position of the object from an alignment reference position and a displacement quantity in the arrangement direction, and controls to drive the stage in the direction XY and the rotational direction in accordance with the displacement quantities;

wherein the inspection equipment inspects with respect to the object on the stage.

2. The alignment apparatus according to claim 1, wherein the stage has:

a holding stage which holds the object; and an XY stage which moves the holding stage in respective directions orthogonal to each other.

3. The alignment apparatus according to claim 2, wherein the holding stage has:

a rotary stage which is provided on an inner periphery so as to be capable of moving up and down and can rotate while sucking and holding the object; and a suction holding stage which is provided on an outer periphery of the rotary stage, and sucks and holds the entire surface of the object.

4. The alignment apparatus according to claim 2, wherein the holding stage forms a notch portion and a hole portion used to detect an outer peripheral edge according to a size of the object by using the sensor.

5. The alignment apparatus according to claim 1, wherein the sensor has:

a light projecting element which projects the light; and a light receiving element which outputs a signal on a level corresponding to a light quantity of the light which is projected from the light projecting element and incident thereupon without being blocked by the outer peripheral edge of the object.

6. The alignment apparatus according to claim 1, wherein a plurality of the sensors are provided in accordance with a size of the object.

7. The alignment apparatus according to claim 1, wherein the stage has a holding stage which rotatably holds the object and an XY stage which moves the holding stage in respective directions orthogonal to each other, and the sensor is provided on the XY stage and detects the outer peripheral edge of the object which rotates by the holding stage.

8. The alignment apparatus according to claim 7, wherein the stage can move between a delivery position for the object and a predetermined position where the inspection is carried out in the equipment, and the sensor detects the outer peripheral edge of the object in a period after the stage receives the object at the delivery position until it moves to the predetermined position.

9. The alignment apparatus according to claim 1, further comprising a buffer holding portion which is provided on a carriage path of the object between the carriage robot and the stage and holds a plurality of the objects.

10. The alignment apparatus according to claim 9, wherein the buffer holding portion is a swiveling arm having at least two carnage arms.

11. The alignment apparatus according to claim 9, wherein the buffer holding portion is a swiveling arm having a rotary shaft and three carriage arms provided with respect to the rotary shaft at equal angles.

12. The alignment apparatus according to claim 11, wherein the swiveling arm moves each of the carriage arms to circulate to an object delivery position, a macro inspection position, and a micro inspection delivery position.

13. The alignment apparatus according to claim 1, wherein the inspection equipment is an inspection apparatus for a semiconductor wafer.

14. The alignment apparatus according to claim 1, wherein the object is a semiconductor wafer.

15. An alignment apparatus comprising:

an XYθ stage which is provided to a wafer inspection apparatus which performs a micro inspection for a semiconductor wafer, and also functions as a stage of the micro inspection and holds the semiconductor wafer delivered by a carriage robot by full suction, and performs a movement operation for the semiconductor wafer in a direction XY and a rotation operation in a direction θ, the XYθ stage forming a notch portion and a hole portion at positions corresponding to each wafer edge according to a size of the semiconductor wafer;

a swiveling arm which is provided on a carriage path of the semiconductor wafer between the carriage robot and the XYθ stage and has three carriage arms which hold three of the respective semiconductor wafers, the swiveling arm moving each of the carriage arms to circulate to a delivery position of the semiconductor wafer, a macro inspection position and a micro inspection delivery position;

respective sensors provided at respective positions corresponding to the notch portion and the hole portion and detect a wafer edge of the semiconductor wafer rotating by the rotation operation of the XYθ stage, each of the sensors having a light projecting element which projects the light and a light receiving element which outputs a signal on a level corresponding to a quantity of the light incident thereupon without being blocked by the wafer edge of the semiconductor wafer; and an alignment control portion which obtains a central position displacement of the semiconductor wafer with respect to an alignment reference position and a displacement quantity in a direction of a notch or an original flat of the semiconductor wafer based on positional information of the wafer edge of the semiconductor wafer detected by any one of the respective sensors, and at the time of micro inspection controls to move the XYθ stage in the direction XY and the direction θ so as to eliminate the central position displacement and the displacement quantity in the direction of the notch or the original flat, thereby aligning the semiconductor wafer to the alignment reference position;

wherein the wafer inspection apparatus inspects the semiconductor wafer on the XYθ stage.

* * * * *